United States Patent [19]
Carter

[11] Patent Number: 5,646,709
[45] Date of Patent: Jul. 8, 1997

[54] PORTABLE HAND-HELD PUPILLOMETER WITH DYNAMIC ELECTRONIC IMAGE CENTERING AID AND METHOD OF USE THEREOF

[75] Inventor: Elbert P. Carter, Wilmington, Del.

[73] Assignee: Fairville Medical Optics, Inc., Mendenhall, Pa.

[21] Appl. No.: 424,679

[22] Filed: Apr. 18, 1995

[51] Int. Cl.$^6$ .................................................. A61B 3/10
[52] U.S. Cl. ................................... 351/218; 351/205
[58] Field of Search .................................. 351/205, 206, 351/218, 216, 200, 211, 221, 246

[56] References Cited

U.S. PATENT DOCUMENTS 4,755,043  7/1988  Carter ........................... 351/205
5,187,506  2/1993  Carter ........................... 351/221

*Primary Examiner*—Hung X. Dang
*Attorney, Agent, or Firm*—Duane, Morris & Heckscher

[57] ABSTRACT

Portable hand-held pupillometers for characterizing a subject's pupil which are operated by a user. The hand-held pupillometer comprise optical units for dynamically imaging the subject's pupil, and centering units interfaced and operated by the user for centering the subject's pupil on the optical unit in preparation for imaging the subject's pupil. The hand-held pupillometers taught herein allow a user of the system to accurately and efficiently obtain an image of the subject's pupil which may be particularly useful for the diagnosis of Alzheimer's disease. The centering unit may also be used to display messages or pupil size and dynamic response data to the user in an easily read and useable format.

20 Claims, 24 Drawing Sheets

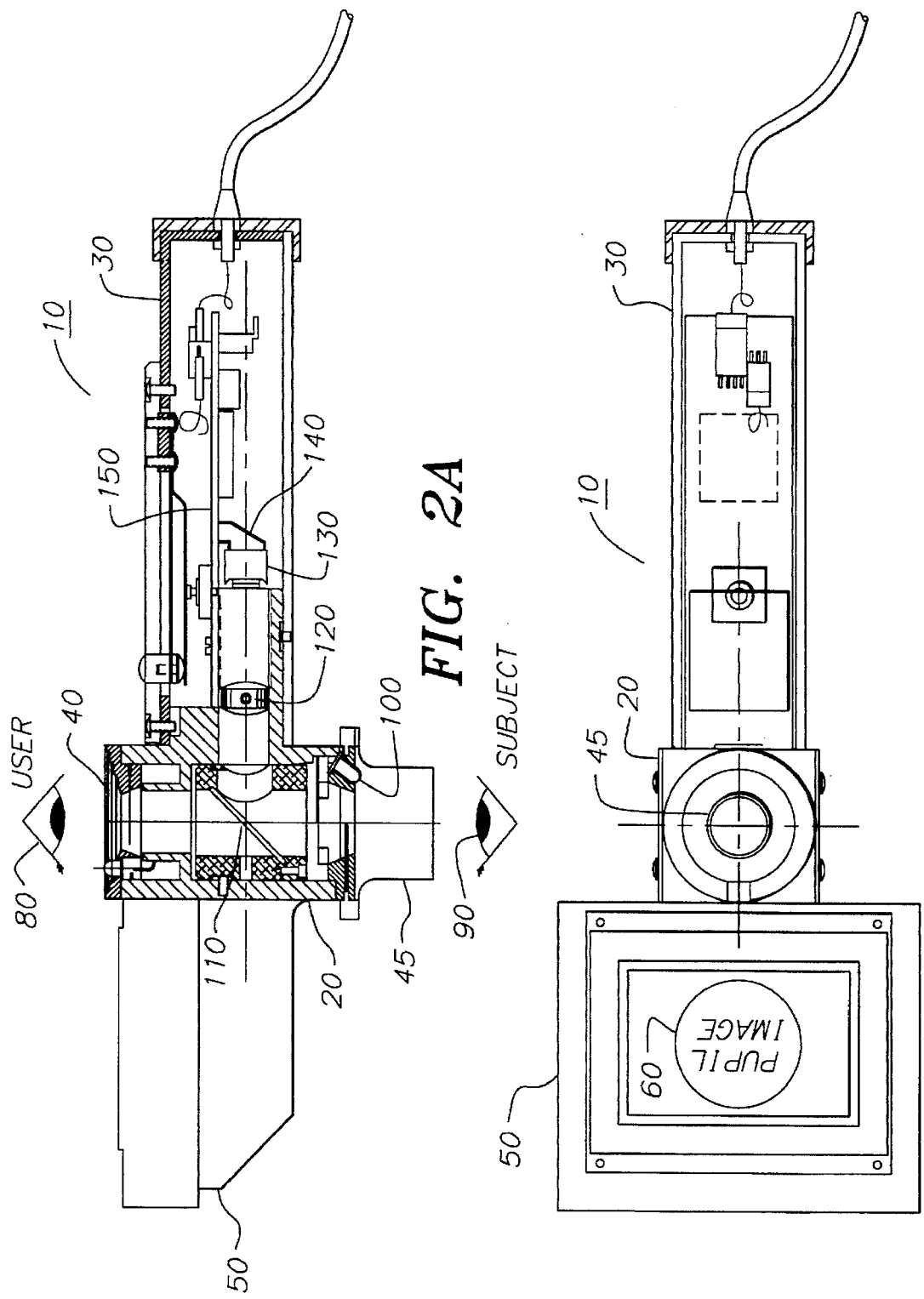

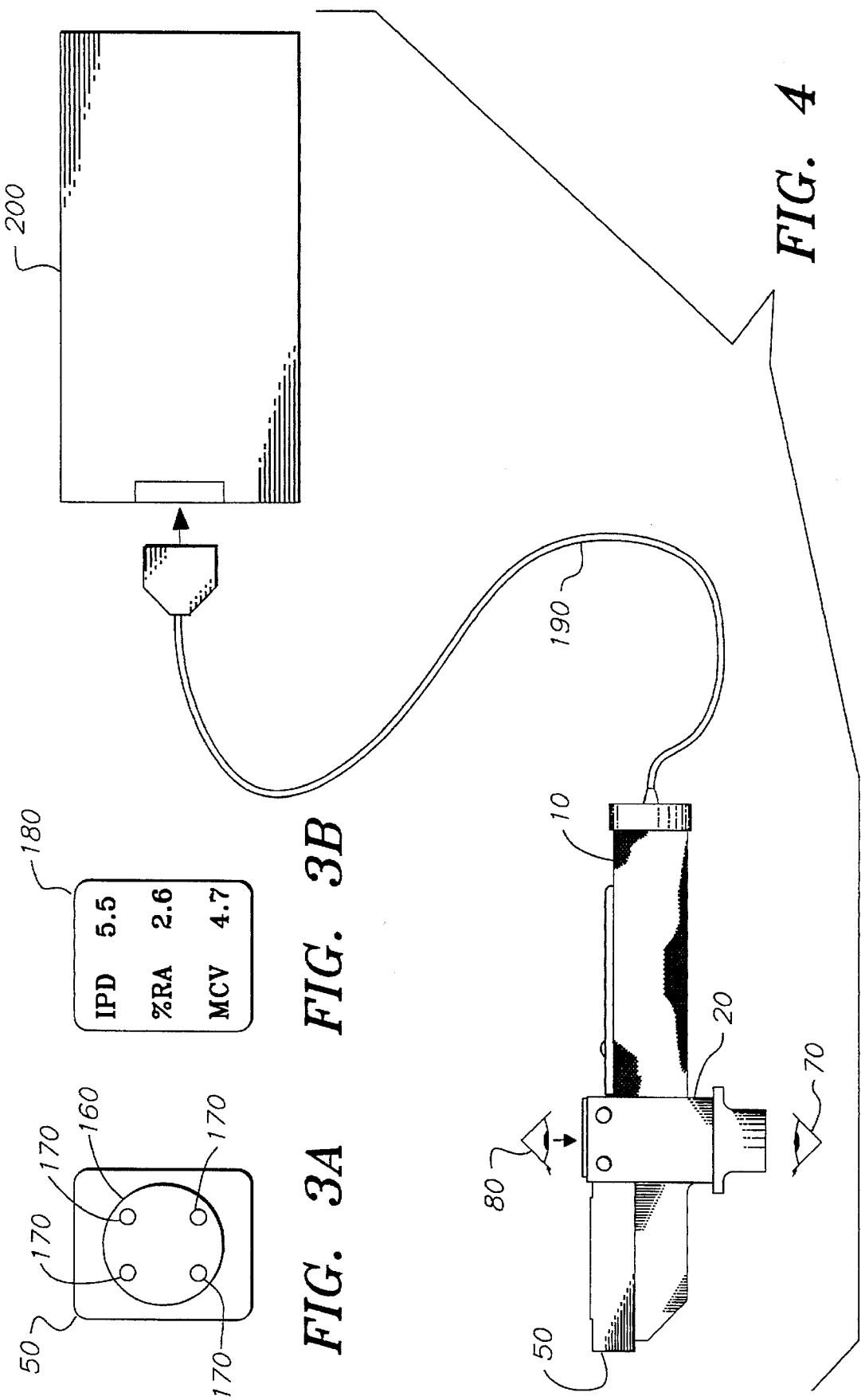

FIFO BOARD

FIFO BOARD

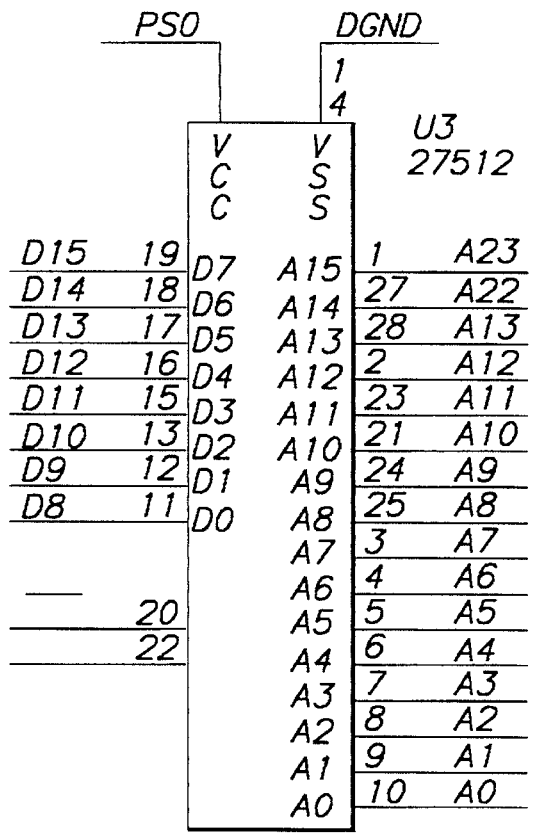
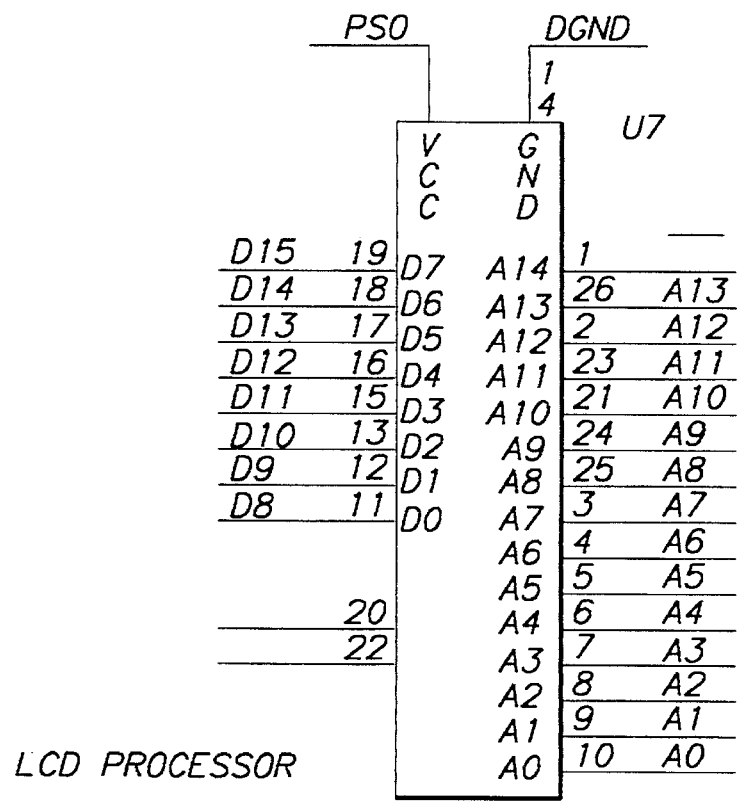
LCD PROCESSOR
FIG. 5G

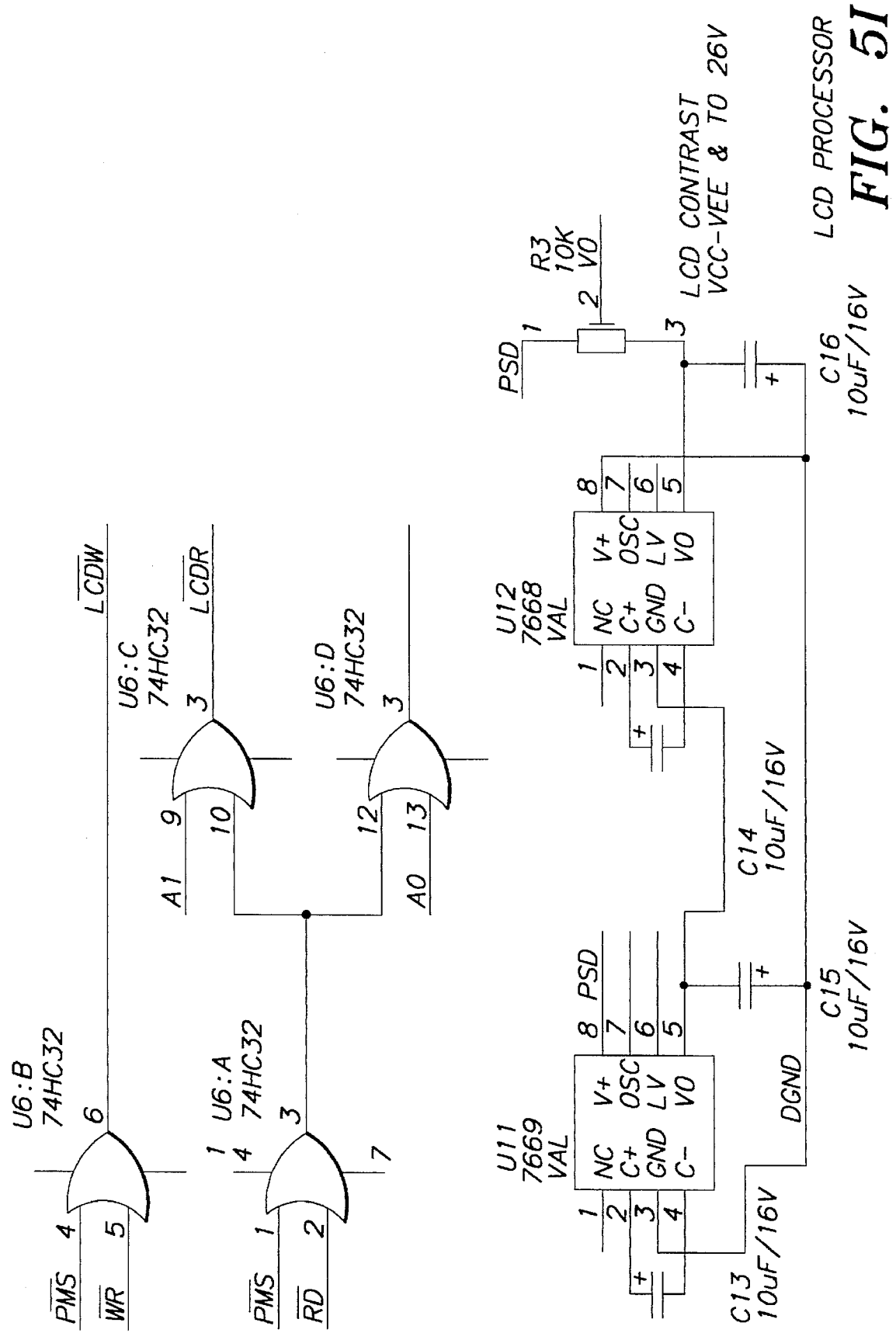
FIG. 5I LCD PROCESSOR

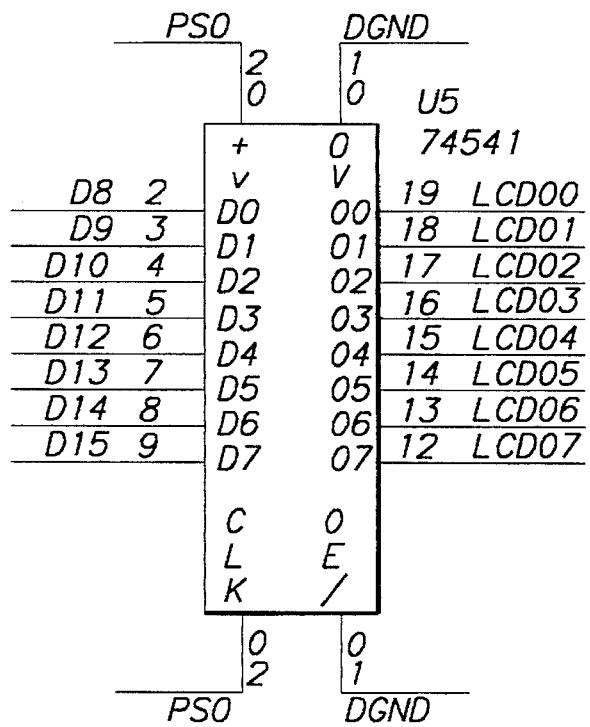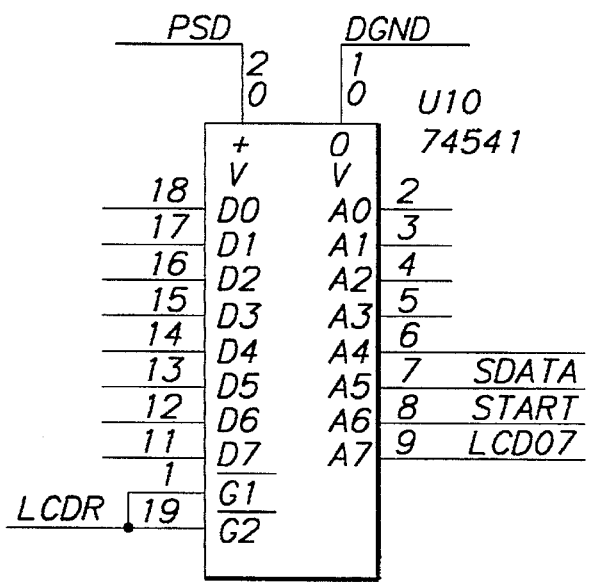
LCD PROCESSOR
FIG. 5J

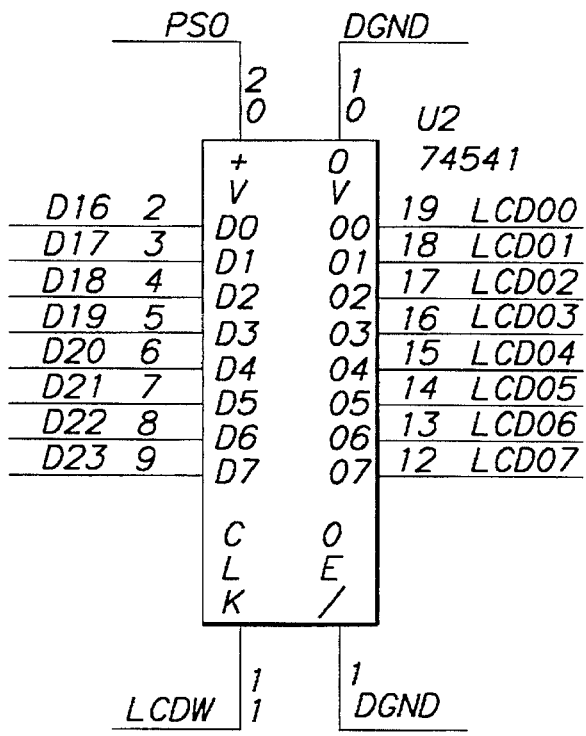
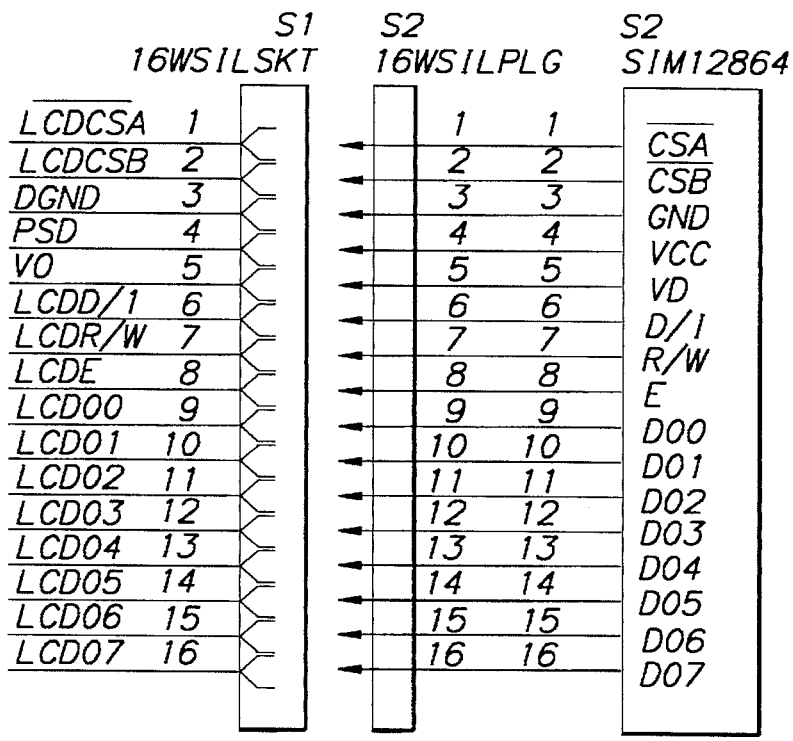
LCD PROCESSOR
FIG. 5K

PCMCIA PUPILLOMETER

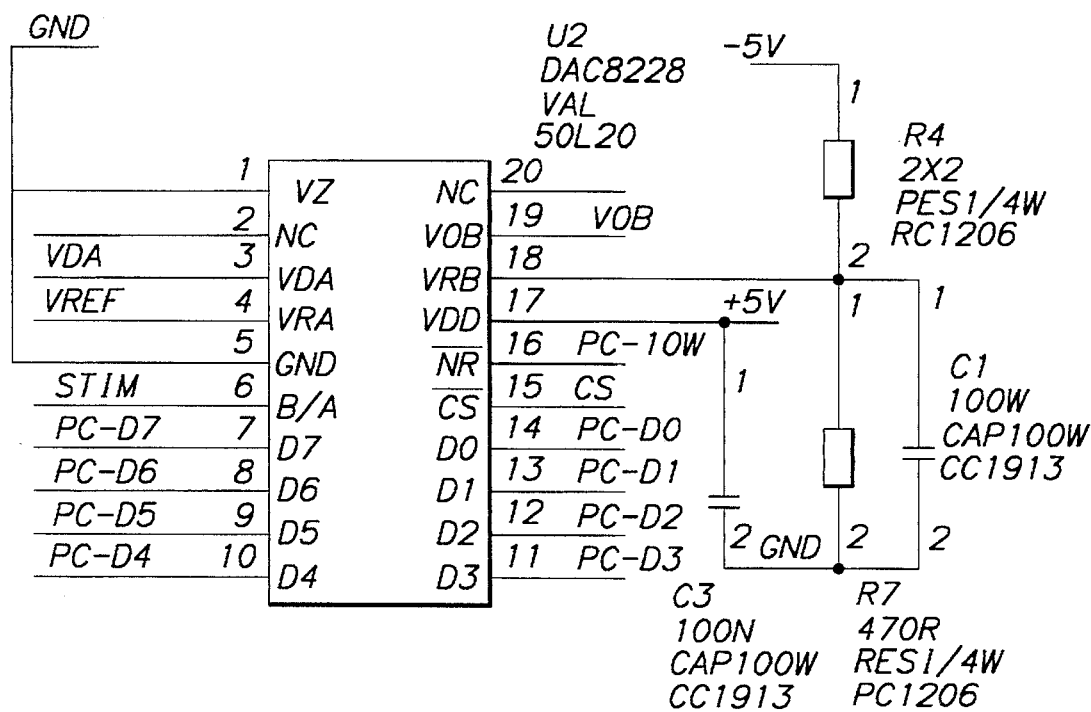
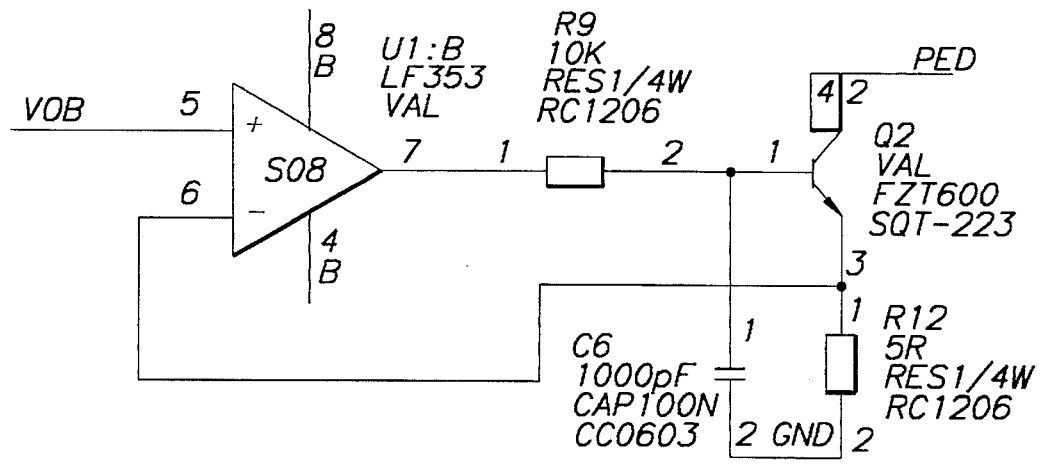
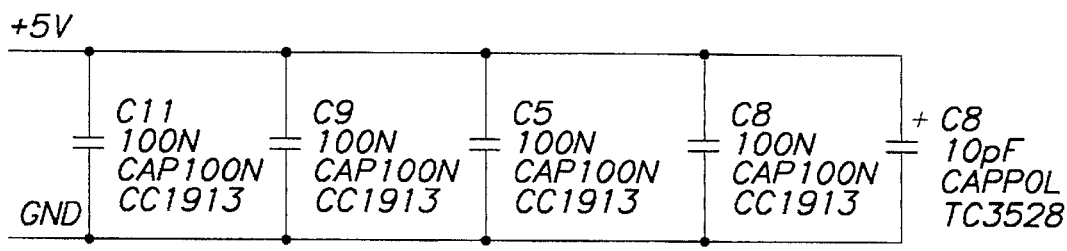
PCMCIA PUPILLOMETER
FIG. 5M

| | | | |
|---|---|---|---|
| GND | 68 | 34 | GND |
| | 67 | 33 | |
| | 66 | 32 | PC-D2 |
| | 65 | 31 | PC-D1 |
| | 64 | 30 | PC-D0 |
| | 63 | 29 | PC-A0 |
| | 62 | 28 | PC-A1 |
| PC-REG | 61 | 27 | PC-A2 |
| | 60 | 26 | |
| | 59 | 25 | |
| | 58 | 24 | |
| | 57 | 23 | |
| | 56 | 22 | |
| | 55 | 21 | |
| | 54 | 20 | |
| | 53 | 19 | |
| | 52 | 18 | |
| +5V | 51 | 17 | +5V |
| | 50 | 16 | |
| | 49 | 15 | |
| | 48 | 14 | |
| | 47 | 13 | |
| | 46 | 12 | |
| PC-IOW | 45 | 11 | |
| PC-IOR | 44 | 10 | |
| | 43 | 9 | |
| | 42 | 8 | |
| | 41 | 7 | |
| | 40 | 6 | PC-D7 |
| | 39 | 5 | PC-D6 |
| | 38 | 4 | PC-D5 |
| | 37 | 3 | PC-D4 |
| | 36 | 2 | PC-D3 |
| GND | 35 | 1 | GND |

PCMCIA PUPILLOMETER

*FIG. 5N*

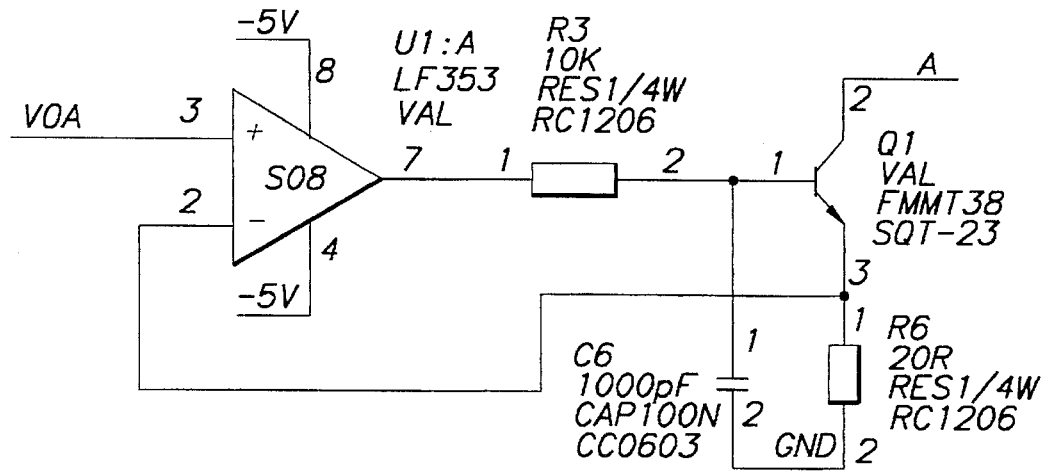
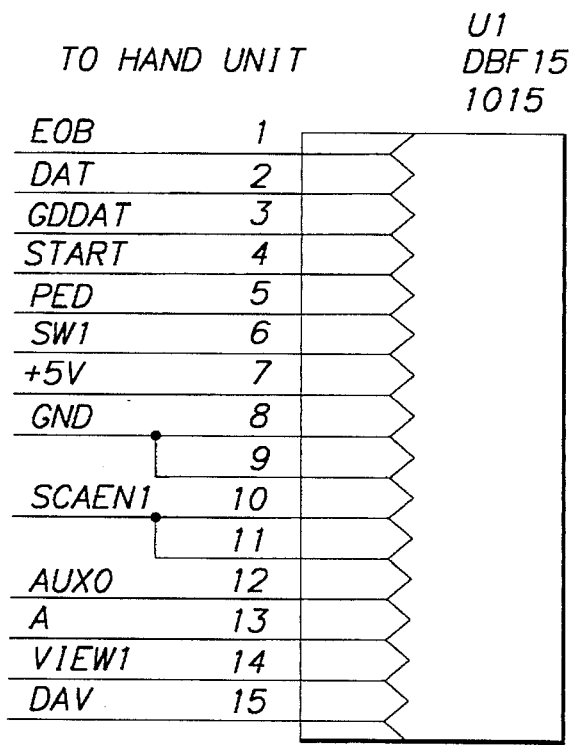
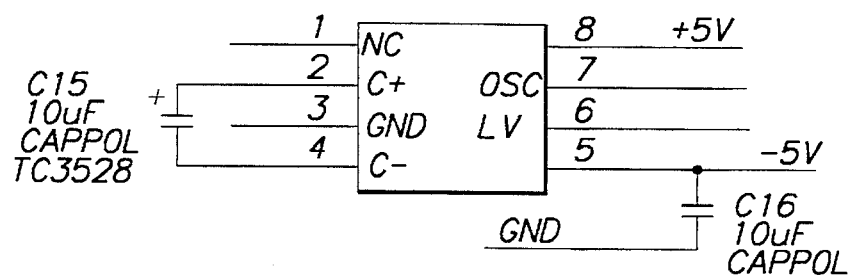
PCMCIA PUPILLOMETER
FIG. 50

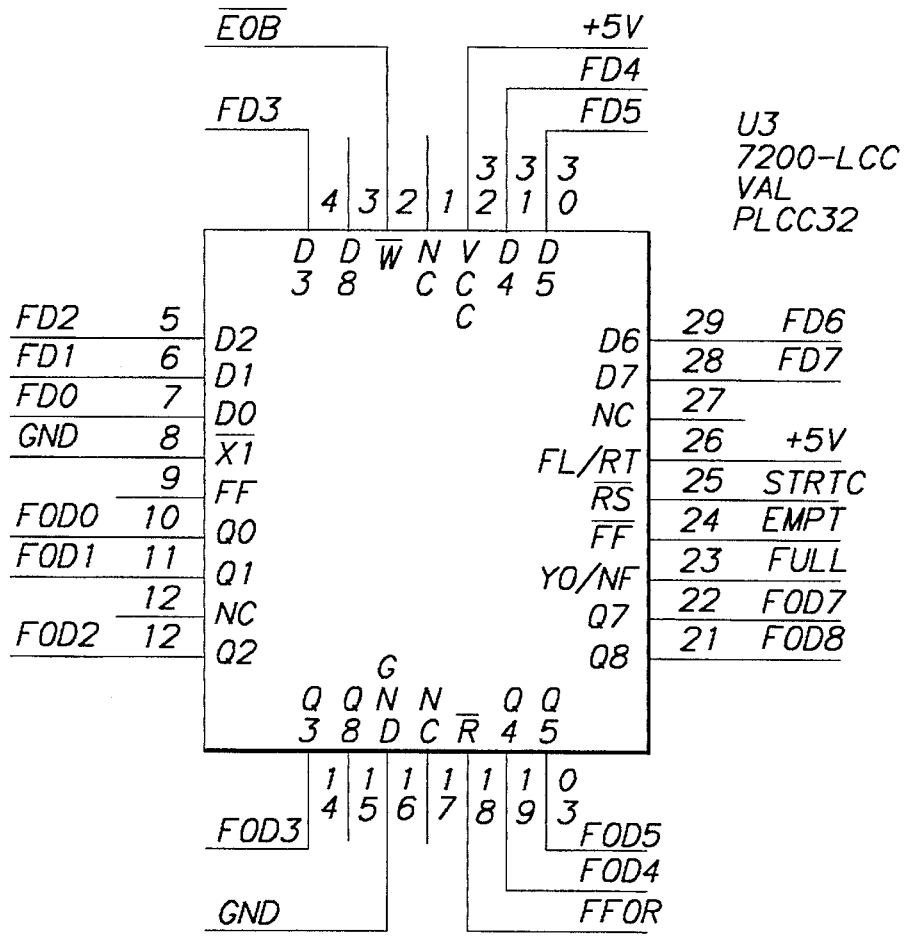
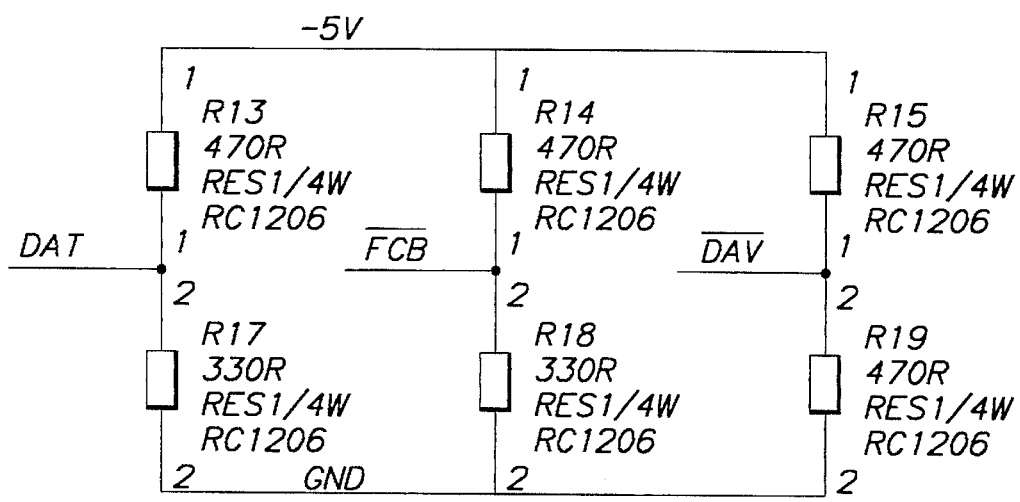
PCMCIA PUPILLOMTER
FIG. 5P

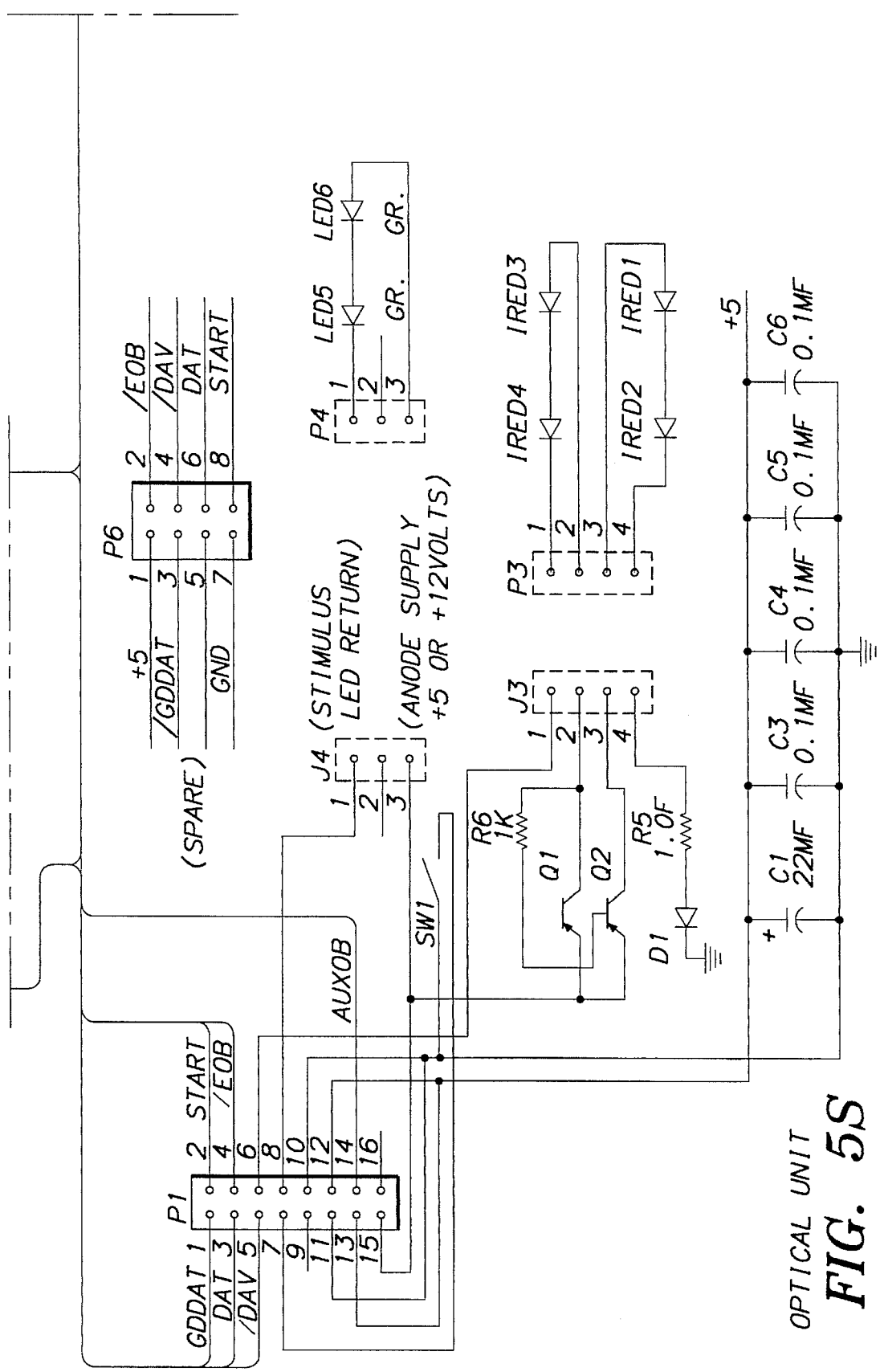
FIG. 5S  OPTICAL UNIT

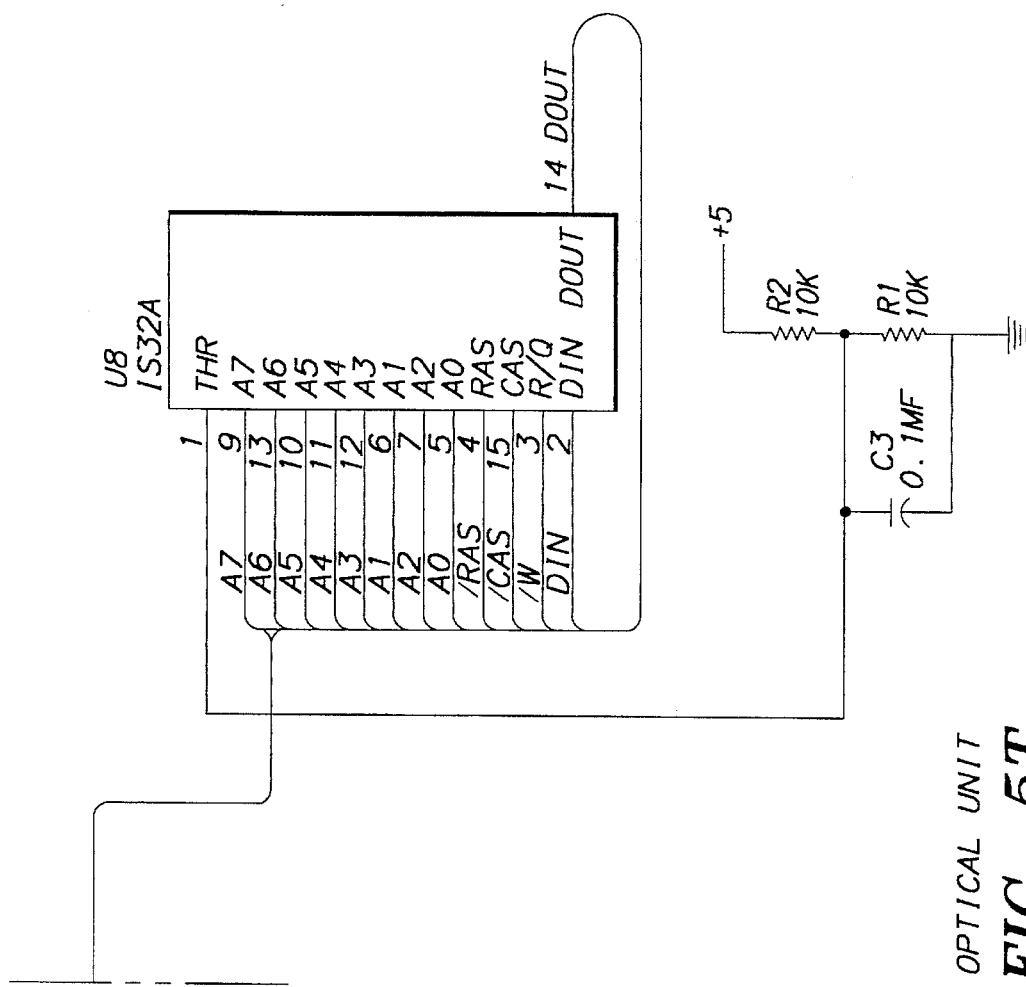
FIG. 5T  OPTICAL UNIT

| IPD  | IPD  | IPD      |
|------|------|----------|
| 6.2  | 6.2  | 6.2      |
| MPD  | RA   | RA       |
| 4.7  | 1.5  | 1.5      |
| RA   | %RA  | TIME     |
| 1.5  | 24   | 14:35:45 |

| IPD      | IPD  | IPD  |
|----------|------|------|
| 6.2      | 6.2  | 6.2  |
| %RA      | MPD  | MPD  |
| 24       | 4.7  | 4.7  |
| TIME     | FPD  | RA   |
| 14:35:45 | 6.0  | 1.5  |

| IPD  | IPD  | IPD  |
|------|------|------|
| 6.2  | 6.2  | 6.2  |
| MPD  | MCV  | RA   |
| 4.7  | 4.7  | 1.5  |
| MCV  | ALT  | ALT  |
| 4.7  | .275 | .275 |

PORTABLE HAND-HELD PUPILLOMETER WITH DYNAMIC ELECTRONIC IMAGE CENTERING AID AND METHOD OF USE THEREOF

FIELD OF THE INVENTION

This invention relates generally to hand-held pupillometers for imaging and measuring a subject's pupil. More specifically, this invention relates to hand-held pupillometers and methods of hand-held pupillometry wherein the pupillometer includes means for displaying an image of the pupil on a display device of an optical unit in the pupillometer to aid the user in centering the optical unit on the pupil.

BACKGROUND OF THE INVENTION

Pupillometry has been discovered to be an effective and useful non-invasive means of characterizing a subject's pupillary response and the condition of the human and animal autonomic nervous system. For example, in U.S. Pat. No. 5,187,506, Carter, it was disclosed therein that narcotics, opiates, depressants, stimulants, alcohol, and both legal and illegal drugs may produce deleterious and destructive effects on an individual's mental and physical performance. Pupillometry as described in the aforementioned patent is useful in detecting such drug or alcohol impairment. The teachings of U.S. Pat. No. 5,187,506, Carter, are specifically incorporated herein by reference. Another useful and effective pupillometer is described in U.S. Pat. No. 4,755,043, Carter. This patent describes a portable, hand-held, dynamic, automatic scanning pupillometer which is operated by a user to view a subject's pupil, and thereby obtain pupil images. The teachings of U.S. Pat. No. 4,755,043 are also incorporated herein by reference.

A main difference between the Carter '506 patent and the Carter '043 patent is that the pupillometer of the Carter '506 patent is a desktop device which may be totally operated by an alert subject whose pupil is to be imaged, while the Carter '043 patent teaches a pupillometer which is operated by a user and can be used to image the pupil of a subject in any posture and any state of alertness or consciousness. A distinct advantage of the pupillometer described in the Carter '506 patent is the incorporation of a self-centering apparatus therein so that the subject can easily and quickly center the image of the pupil on an optical block to form an image thereof. Unfortunately, the pupillometer of the Carter '043 patent does not incorporate aids to centering, and therefore a user of the device described therein must be particularly skilled in operating such a device. Thus a user of the device of the Carter '043 patent can obtain consistent and reliable measurements of pupil size only after practice and considerable painstaking concentration which is fatiguing for both user and subject.

Because of these aforementioned problems and deficiencies, the inventor of the subject matter herein claimed and disclosed has discovered that existing hand-held pupillometers and tabletop pupillometers fail to solve needs in the art for compact, portable devices which provide efficient and active images of a subject's pupil for various purposes under varied conditions of use. Additionally, with the advent of laptop and notebook computers over the last few years, electronic devices such as pupillometers can become even more portable. However, before the conception of the present invention, the art has failed to create circuitry and apparatus to move pupillometers in this direction. Furthermore, the inventor of the claimed pupillometer has found that pupillometry may be particularly useful in diagnosing Alzheimer's disease, and that a hand-held unit could be particularly useful in making such a diagnosis. However, the aforementioned pupillometers and hand-held pupillometers in general do not have the combination of compact size and centering aids to facilitate their use and therefore, do not fulfill a long-felt need in the art for a pupillometer to make accurate, reliable pupil images on subjects in any posture, position or state of alertness. Moreover, the inventor has found that a device used to display an image of the pupil on the optical unit may also display data characterizing pupil size and response to a light stimulus thus providing the user with immediate, easily read and understood dynamic pupil measurement data.

SUMMARY OF THE INVENTION

The aforementioned problems are solved and long-felt needs met by portable hand-held pupillometers provided in accordance with the present invention for characterizing a subject's pupil, which are operated by a user. Preferably, the pupillometers comprise a hand-held optical unit for dynamically imaging the subject's pupil, and a centering unit interfaced to the optical unit and operated by the user for centering the subject's pupil on the optical unit in preparation for imaging the subject's pupil. Methods of characterizing the subject's pupil are also provided in accordance with the present invention. Even more preferably, the methods comprise the steps of viewing the subject's pupil by a user with a hand-held optical unit, centering the subject's pupil on a display device of the hand-held optical unit, and imaging the subject's pupil on the hand-held optical unit, thereby characterizing the subject's pupil.

Hand-held portable pupillometers provided in accordance with the present invention with centering units which allow a user to center a subject's pupil on an optical unit therein provide efficient and accurate pupil images for various pupillometry applications. Hand-held pupillometers in accordance with the present invention are easily portable since they incorporate small, standard sized printed circuit boards which can be interfaced in light, transportable personal laptop computers and notebook computers with sufficient computing power to drive the pupillometers. The pupillometers disclosed and claimed herein may be particularly useful in diagnosing Alzheimer's diseases, which generally is a function of the pupil response when influenced by outside pharmaceutical agents.

The invention will be best understood by those with skill in the art by reading the following Detailed Description of Preferred Embodiments in conjunction with the drawings which are first described briefly below.

BRIEF DESCRIPTION OF THE DRAWINGS

FIGS. 2A and 2B are cross-sectional elevational and plan views respectively of the pupillometer of FIGS. 1A and 1B.

FIGS. 3A and 3B are representations of respectively a pupil display of the optical unit of the pupillometer, and an example of an output of data provided by pupillometers in accordance with the present invention.

FIG. 4 is a schematic view of the pupillometer provided in accordance with the present invention interfaced to a printed circuit card which will be placed in a laptop or notebook computer.

FIGS. 6A through 6I are examples of the pupillometer output provided in accordance with the present invention.

DETAILED DESCRIPTION OF PREFERRED EMBODIMENTS

Figure 1A:
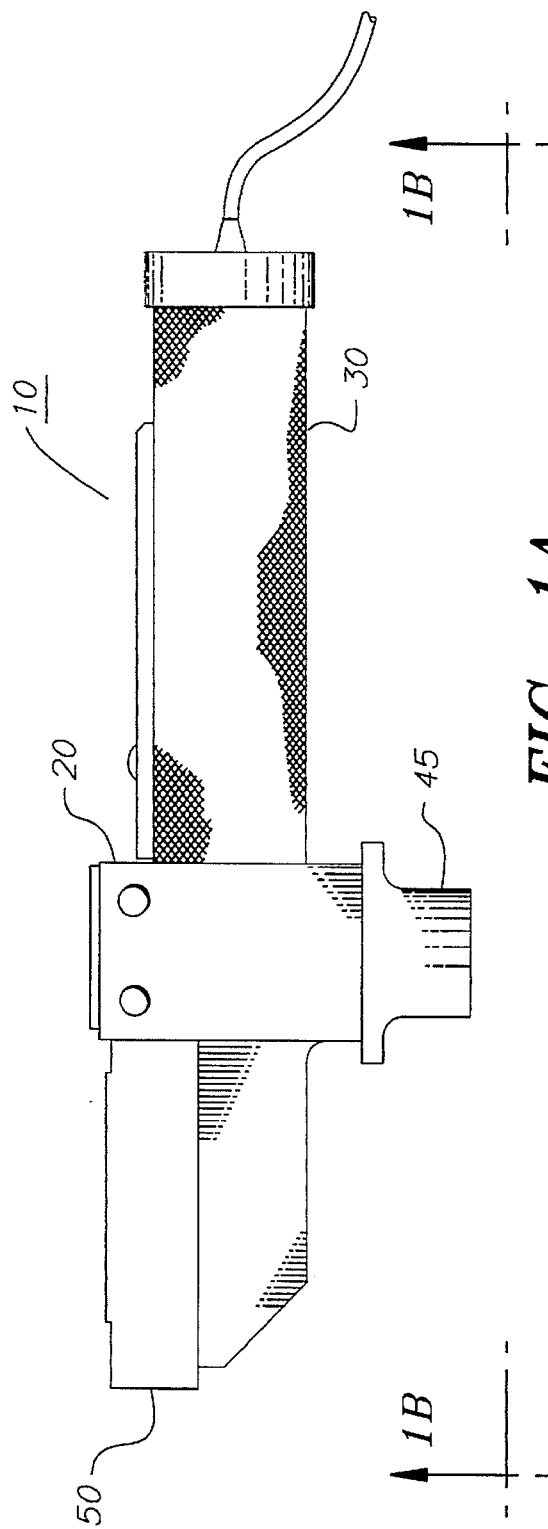
FIGS. 1A and 1B are elevational and plan views respectively of a hand-held pupillometer provided in accordance with the present invention having a centering unit so that a user can center the subject's pupil on a display device of the optical unit of the pupillometer.
Figure 1B:
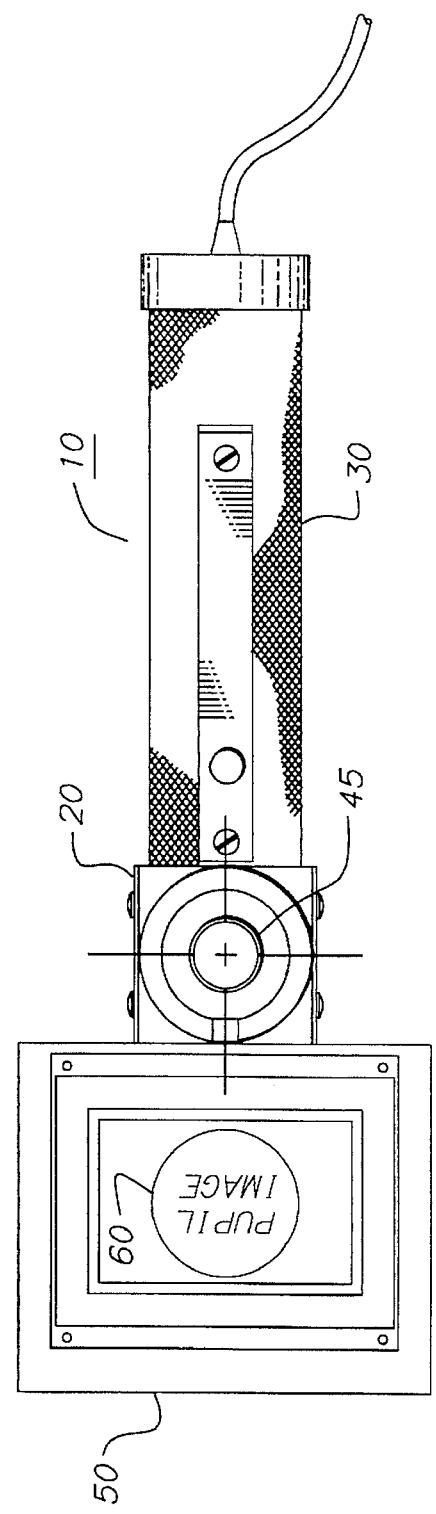

Referring now to the drawings wherein like reference numerals refer to like elements, FIGS. 1A and 1B show a portable hand-held pupillometer 10 provided in accordance with the present invention. The pupillometer 10 of FIGS. 1A and 1B preferably comprises an optical unit shown generally at 20, and a tubular gripping section 30 which houses the optical unit and other elements and electronics which are necessary to operate the pupillometer.

The optical unit 20 further preferably comprises a viewing bore shown generally at 40, through which a user of the pupillometer 10 will view the subject's pupil in order to obtain dynamic images of the pupil. A centering display unit 50 is provided so that a user of the pupillometer 10 can use an enlarged image of the pupil to center a pupil image 60 on the centering display unit 50 which simultaneously centers the pupil image on an imaging device (described below) allowing the user to make an accurate, dynamic image of the pupil as the pupil contracts and dilates in response to a light stimulus provided by the pupillometer as taught by the Carter '043 patent. Preferably, the centering unit 50 is a liquid crystal display (LCD) that is interfaced electronically to the optical unit 20. Even more preferably, the LCD display 50 is commercially available under the trademark SIM 12864 LCD Display.

Referring now to FIGS. 2A and 2B, the cross-sectional elevational and plan views of pupillometer 10 illustrate operation of the pupillometer as a user 80 obtains an image of the subject's 70 pupil 90. The user 80 preferably looks through viewing bore 40 of optical unit 20 to initially line up the optical unit 20 on subject's 70 pupil 90. Infrared emitting diodes 100 illuminate the pupil 90 during stimulation of the pupil by light emitted from diodes which radiate in the visible spectrum. A similar arrangement of green and infrared diodes is illustrated and disclosed in the Carter '506 patent. The subject 70 preferably rests his or her cheek on the cheek rest 45 to steady the device The infrared light reflected from the pupil 90 is split by a beam splitter 110 so that visible light travels to the user's 80 eye and the infrared image is focused by a lens 120 onto the imaging device as described substantially in the aforementioned '043 and '506 Carter patents.

Even more preferably, the infrared image focused by lens 120 falls on an optical semiconductive circuit shown at 130 which digitizes the pupil image by reading the light and dark pixels comprising the pupil image. The optical circuit 130 is interfaced at 140 to a scanning unit 150 which is typically a printed circuit board having scanning software and electronic components which implement the scanning procedures to obtain an image 60 of the pupil 90. A second printed circuit board interfaced to the LCD display 50 preferably also contains a circuit which intercepts the serial video data obtained by the scanning circuit from a computer interface circuit (to be described later) so that the pupil image can be displayed on the LCD display 50. This circuit is called a pupil LCD processor.

Figure 5A:
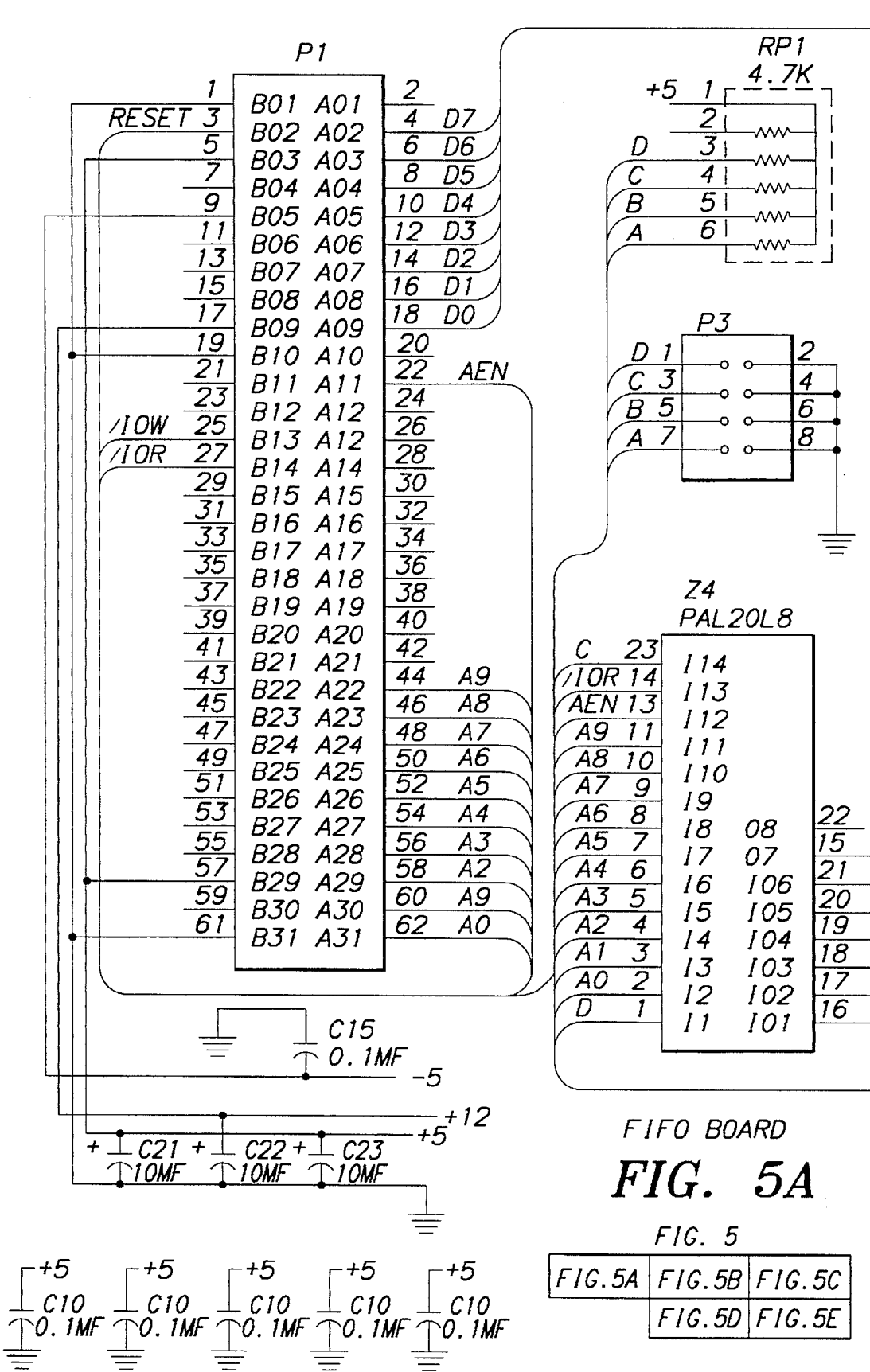
FIGS. 5 and 5A through 5T are schematics of an interface board conforming to the Personal Computer Memory Card International Association (PCMCIA) standard, a scanning circuit, an LCD processor, an optical unit, and a first-in-first-out data circuit in the pupillometer of the present invention.
Figure 5B:
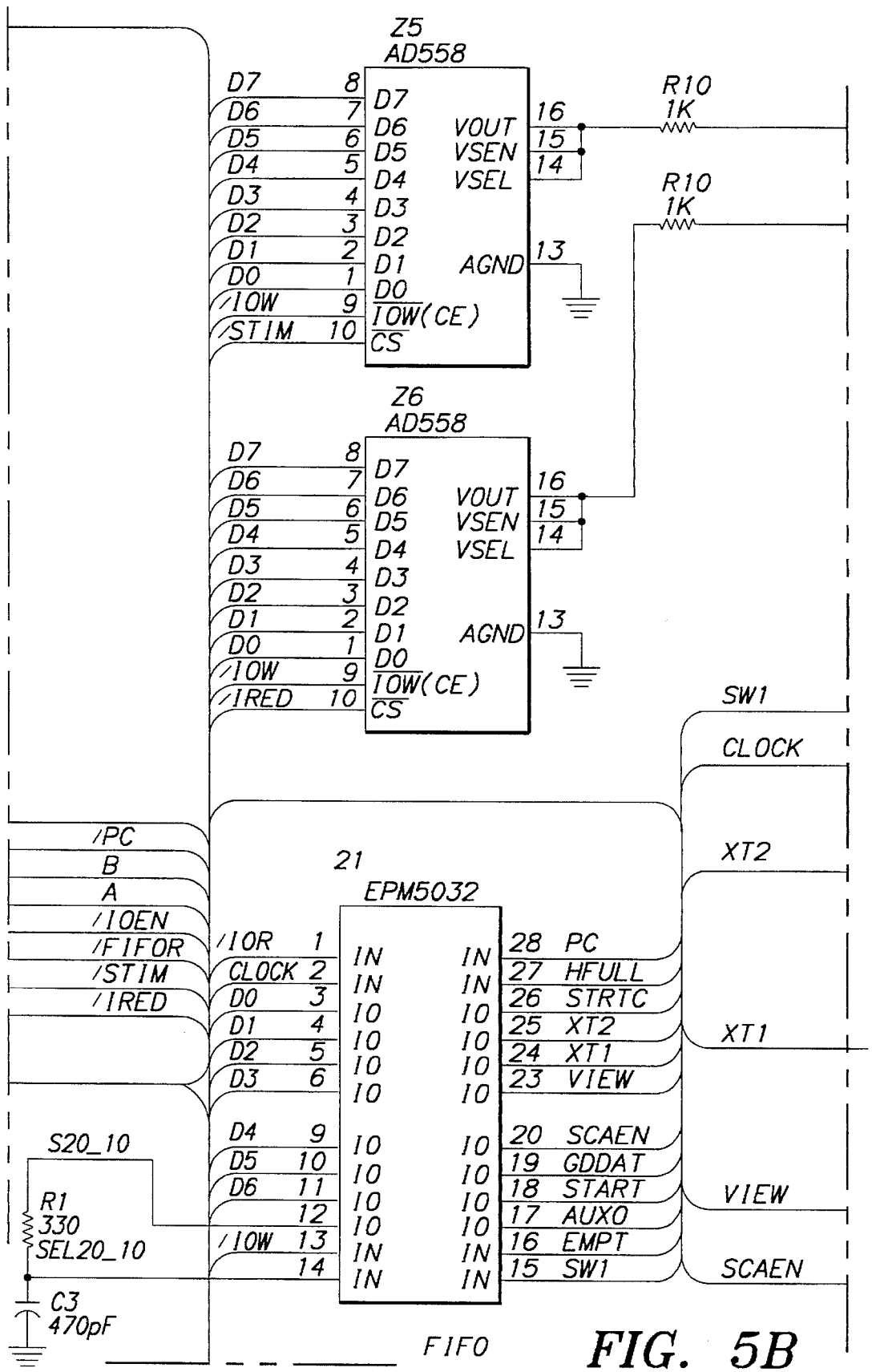
Figure 5C:
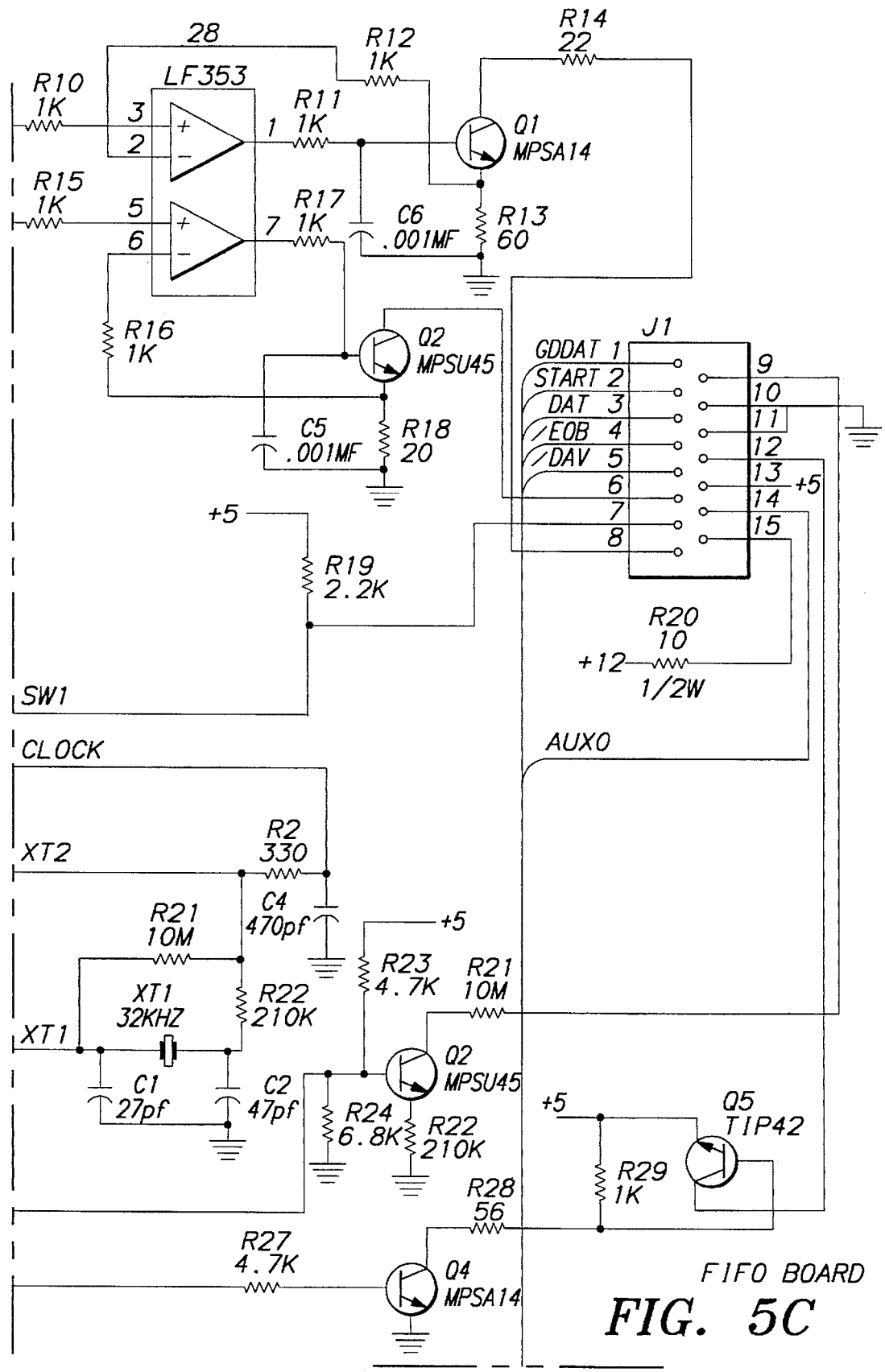
Figure 5D:
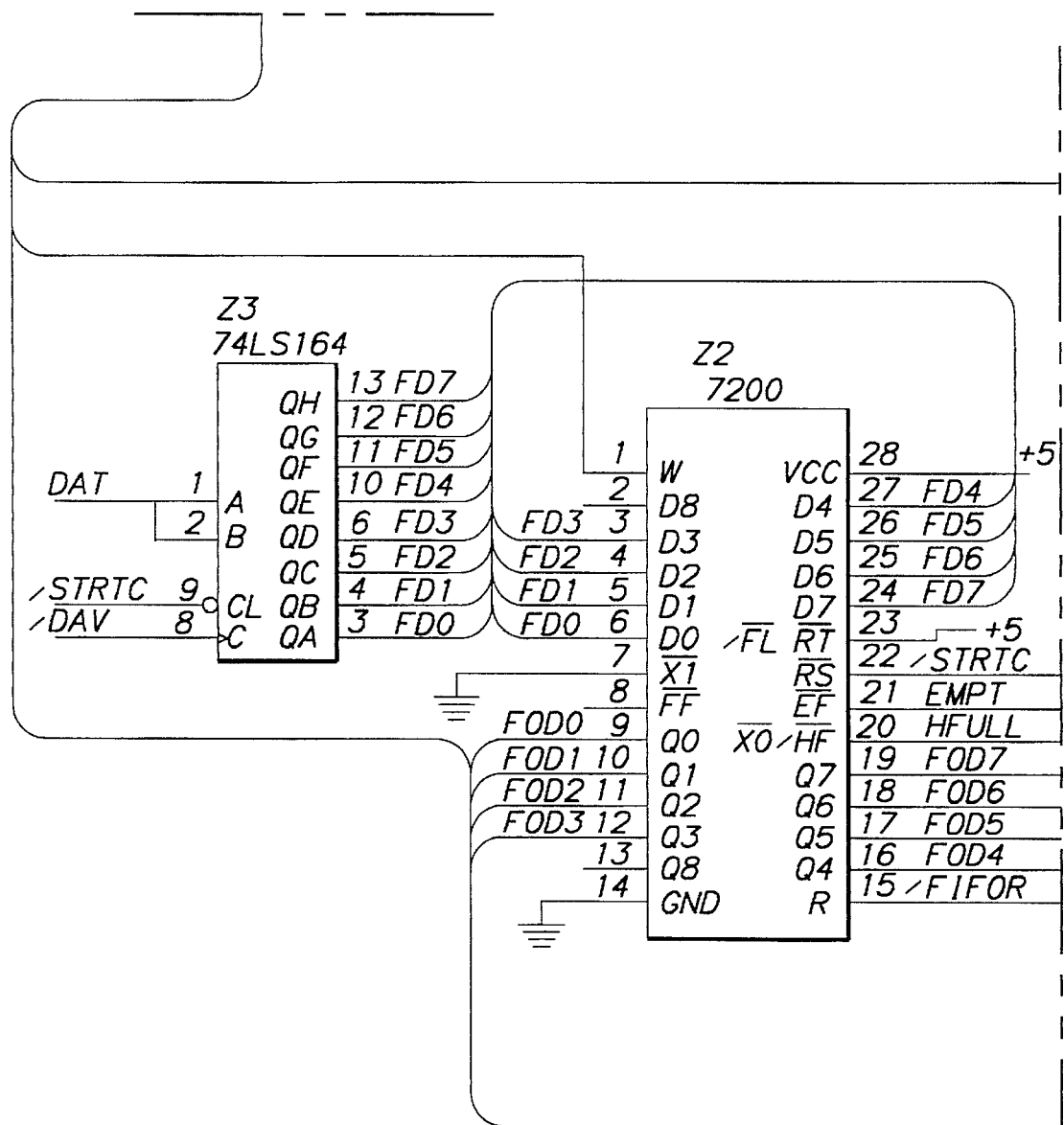
Figure 5E:
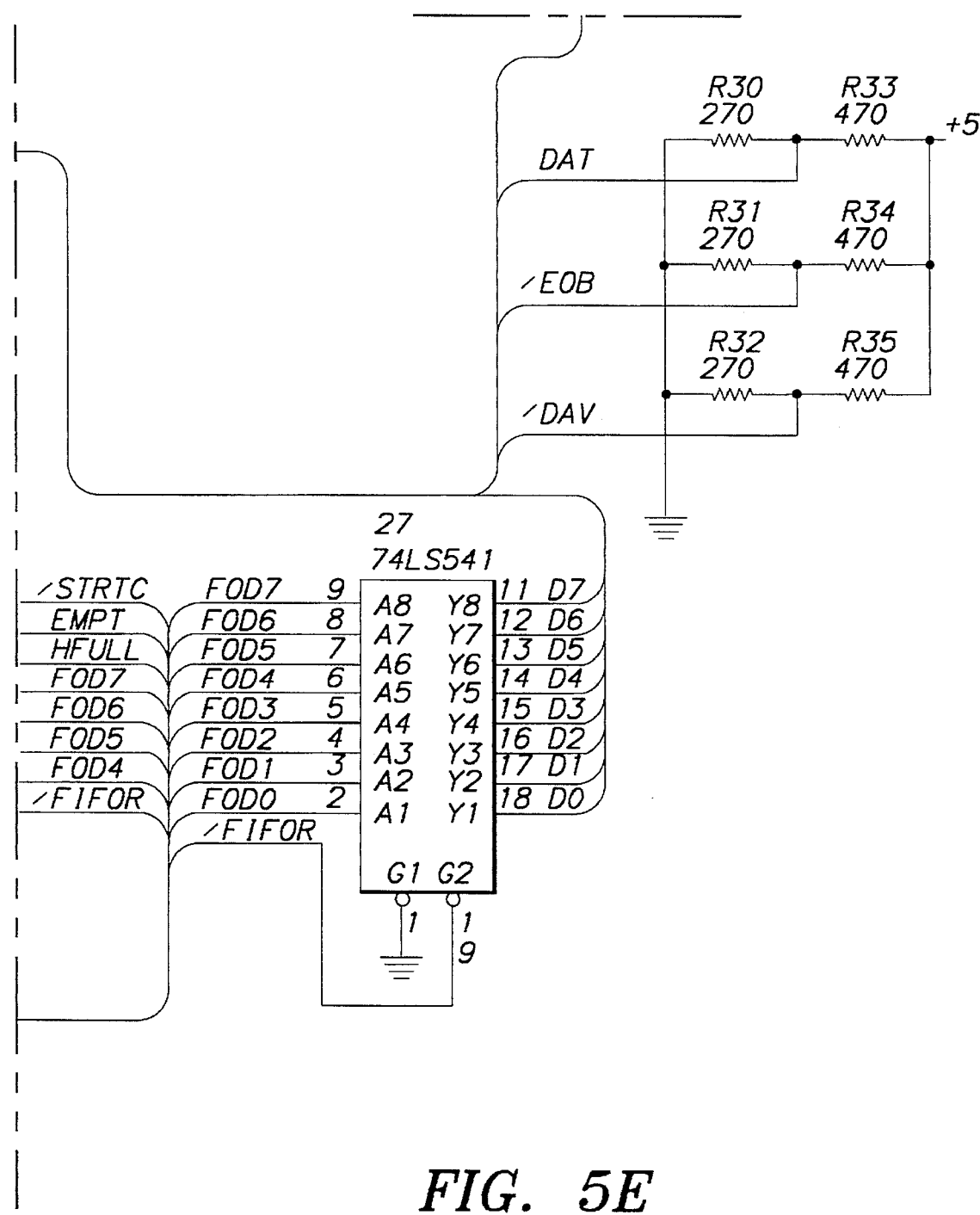
Figure 5F:
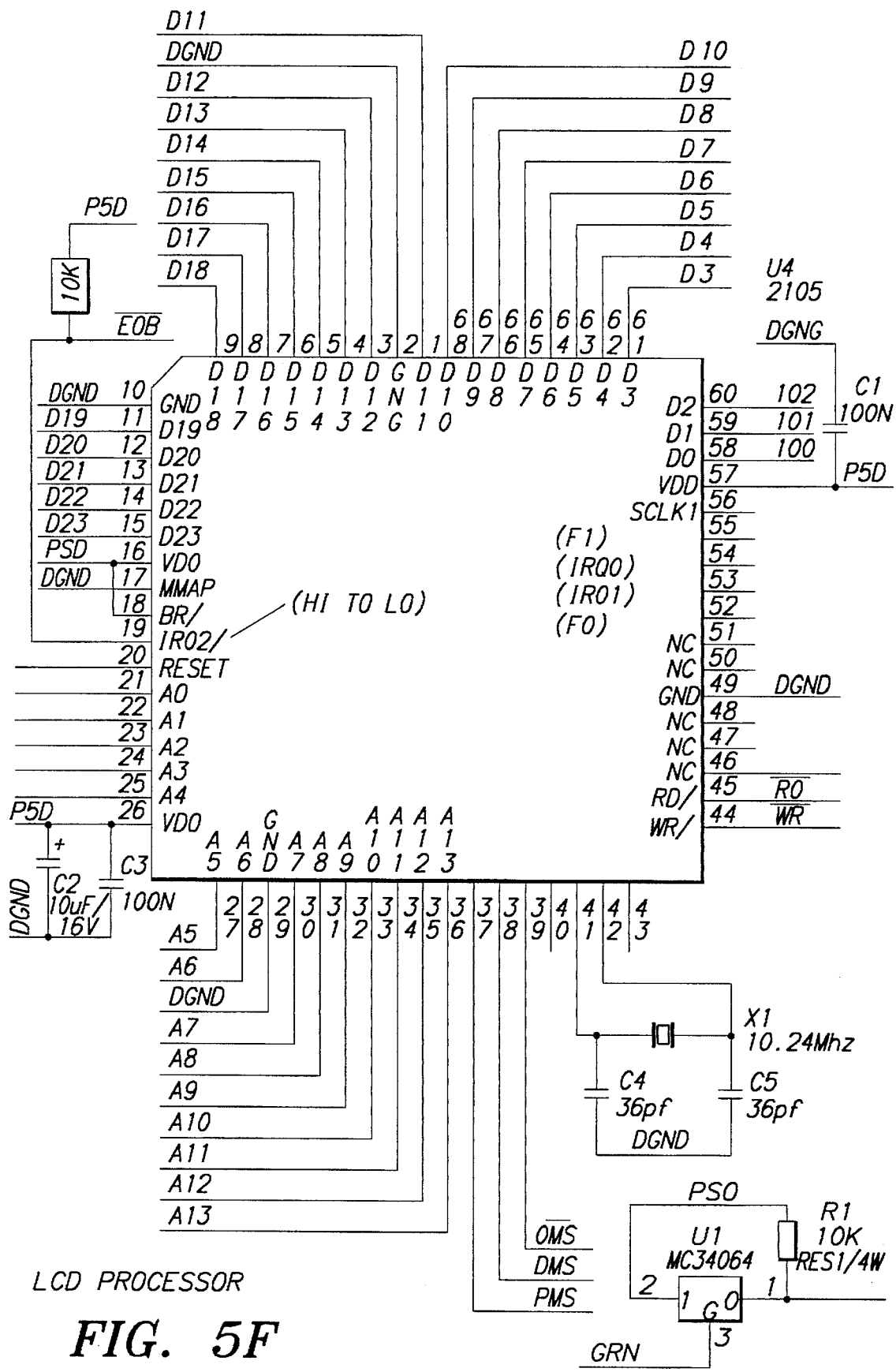
Figure 5H:
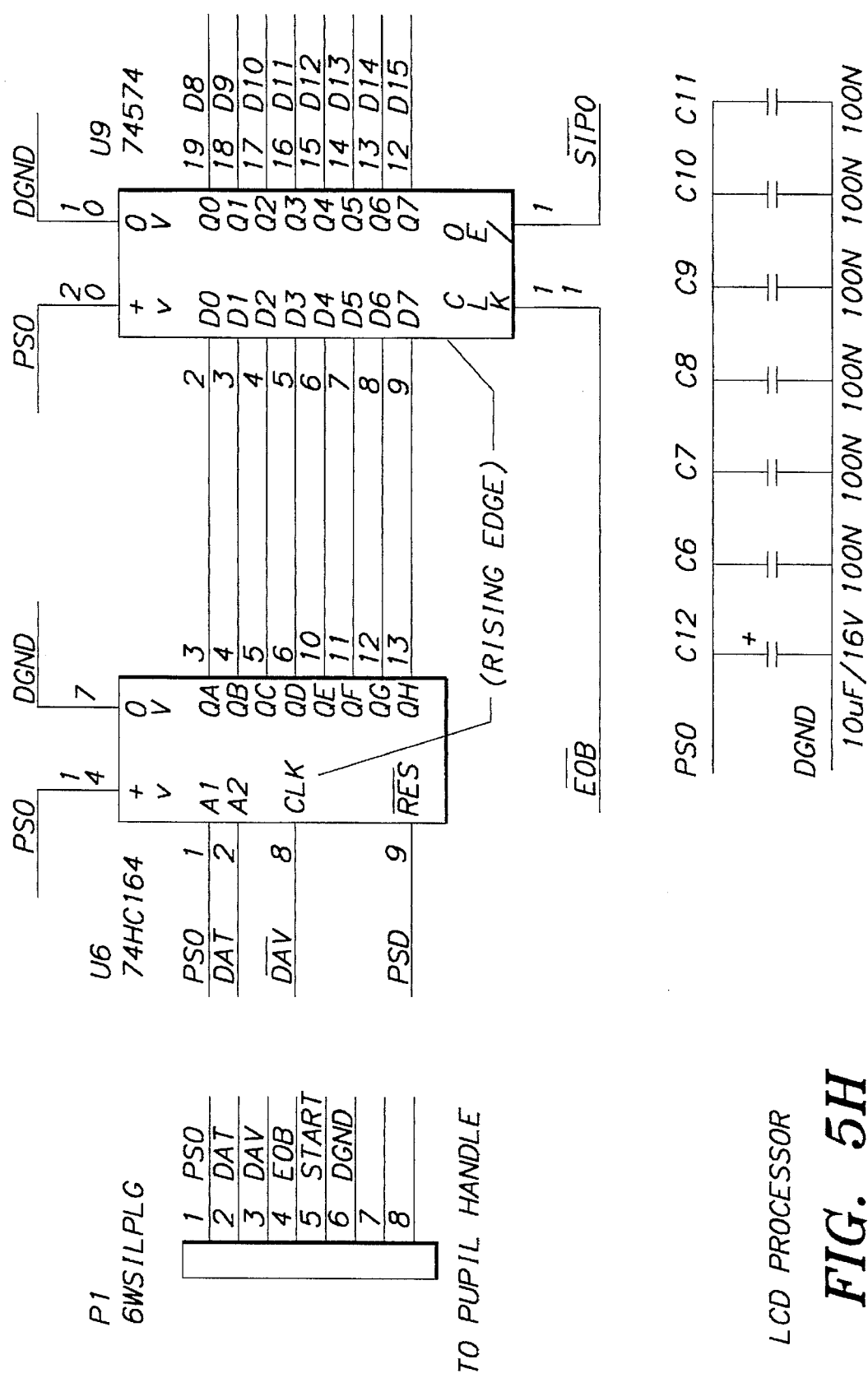
Figure 5L:
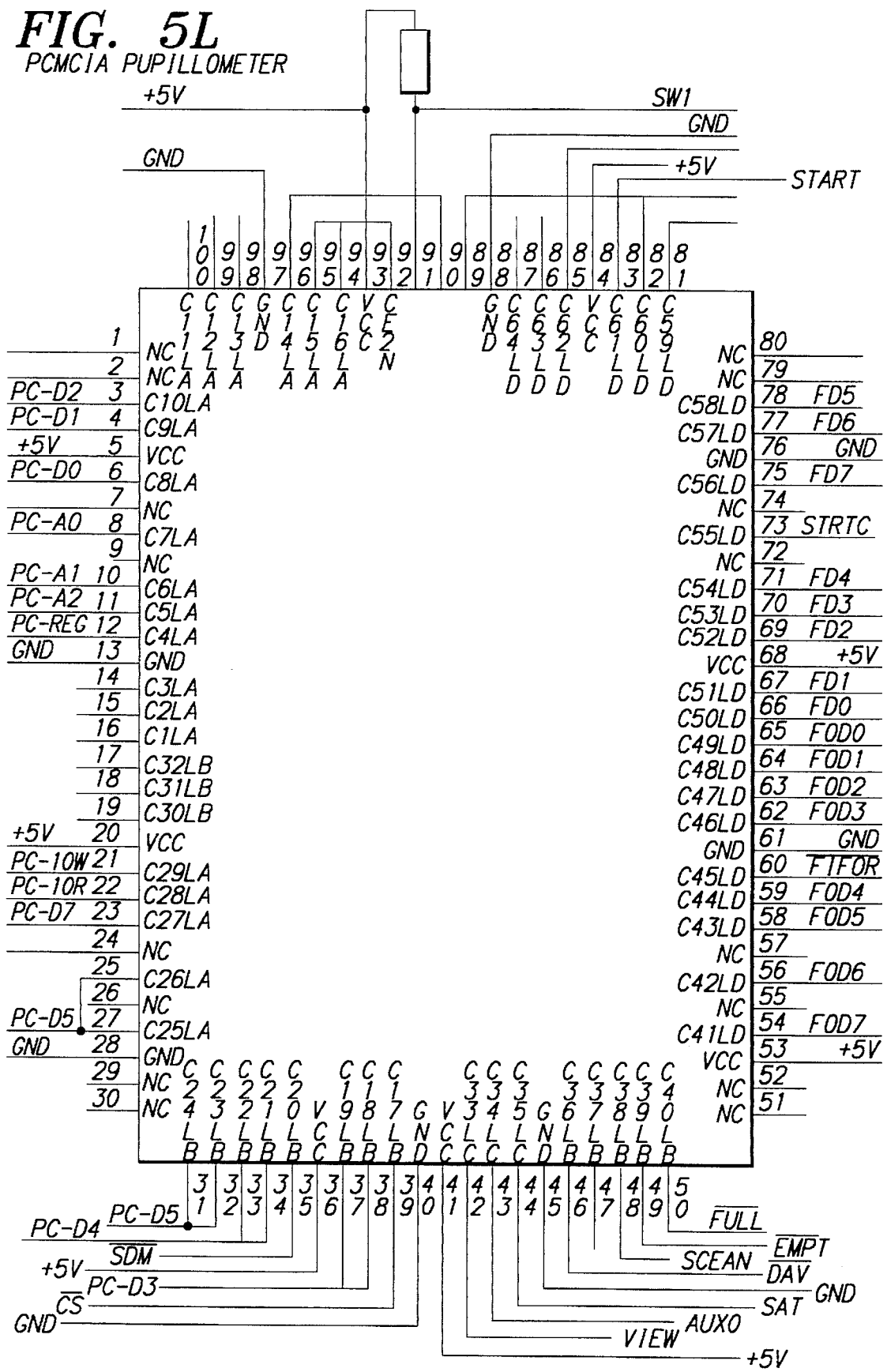
Figure 5Q:
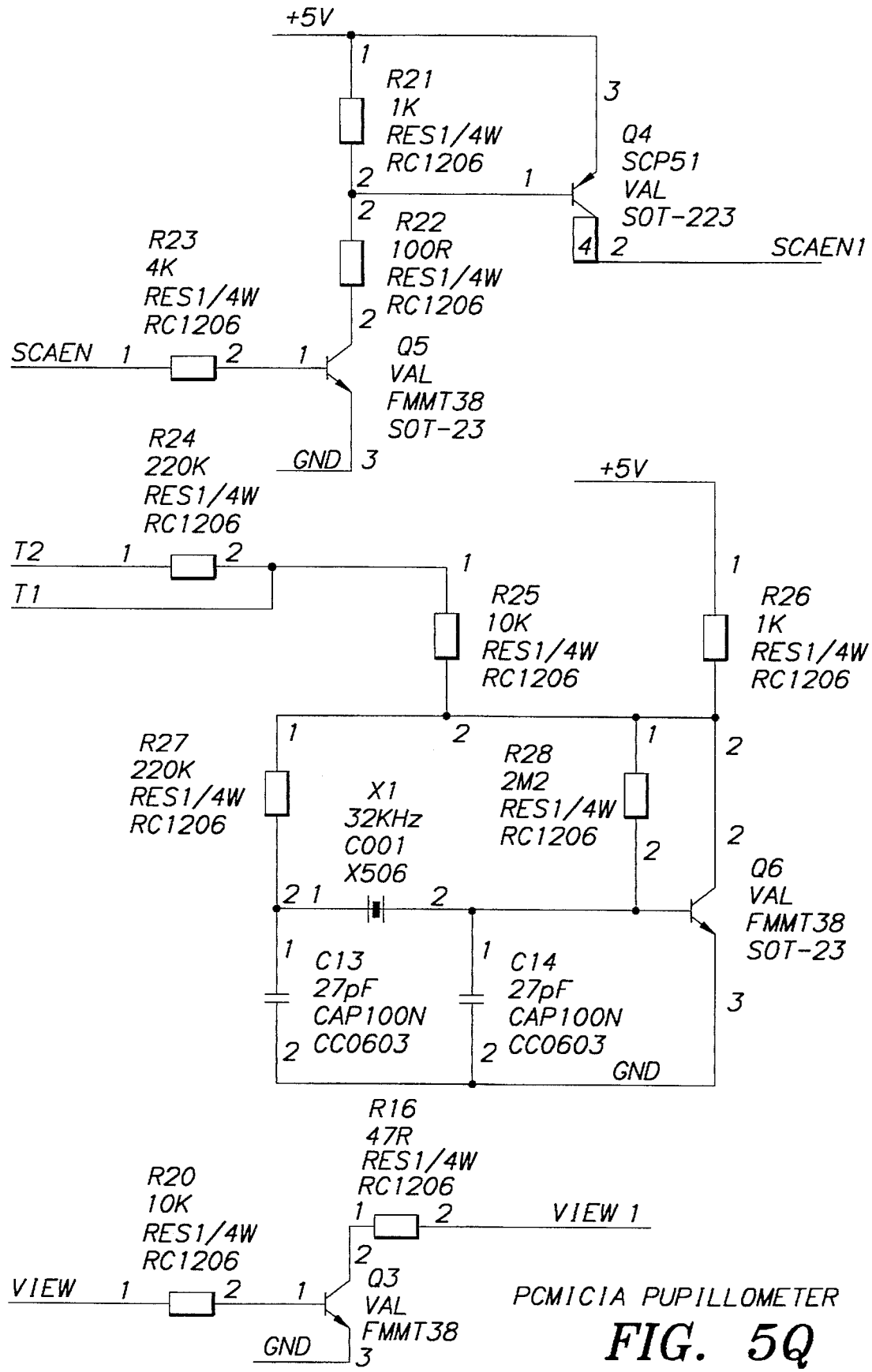
Figure 5R:
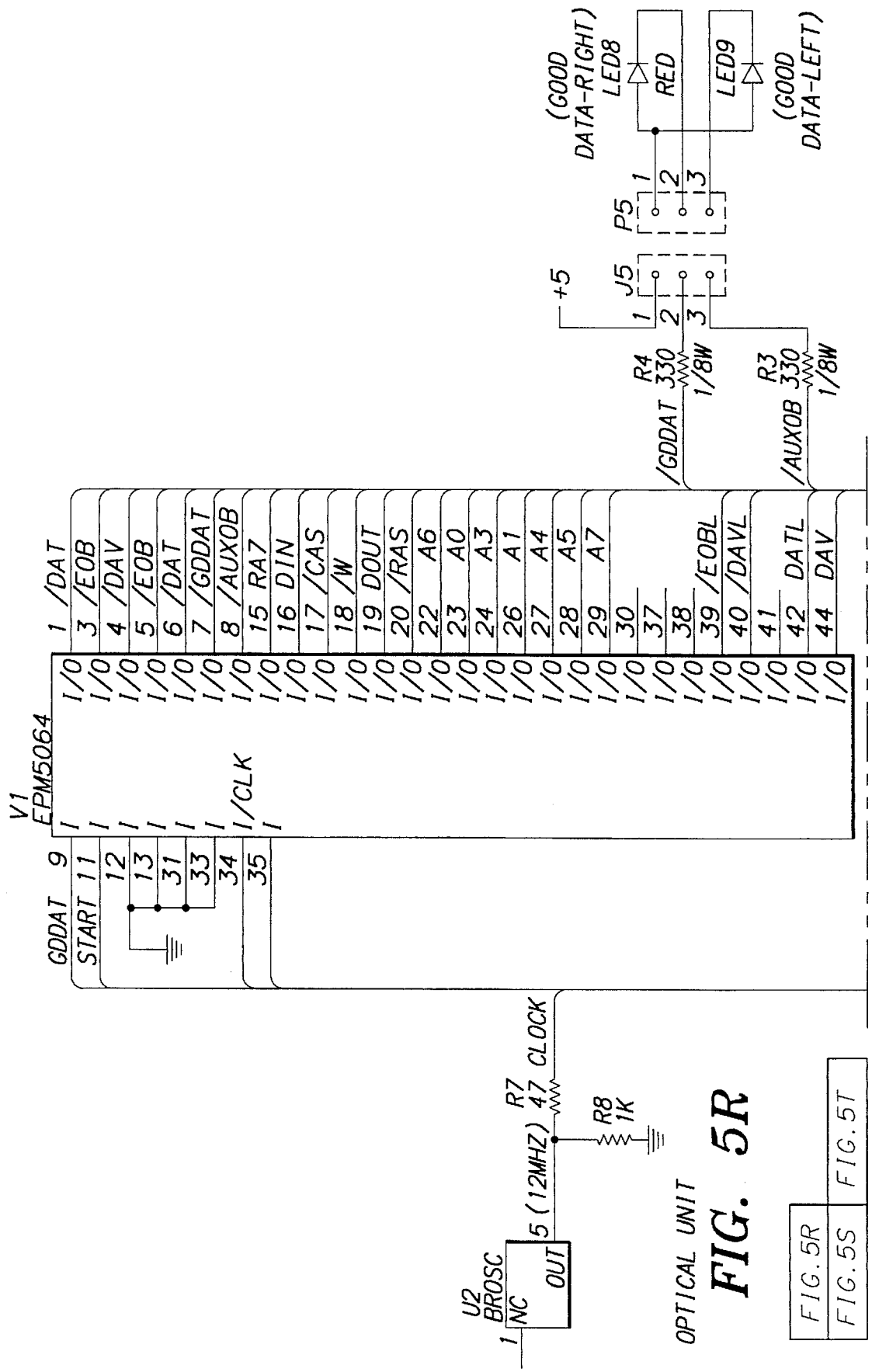

The LCD processor is shown schematically in FIGS. 5F through 5K. Circuitry associated with the optical unit 20 is shown schematically in FIGS. 5R through 5T. The scanning board which implements a first-in-first-out (FIFO) function for the serial data comprising a pupil image is shown schematically in FIGS. 5A through 5E. Finally, a preferred embodiment of a PCMCIA Type II format printed circuit card for driving the pupillometer and which preferably is interfaced in a laptop or notebook computer is shown schematically in FIGS. 5L through 5Q. The circuit schematics of FIGS. 5A through 5T collectively show how the electronic and optical elements found in the pupillometer of the present invention interact to obtain pupil images.

The LCD processor referenced above is a serial to parallel converter which takes serial video data and allows each byte to be read by a digital signal processor (DSP) in the LCD processor. The DSP includes electronic programmable read-only memory (EPROM) and random access memory (RAM), as well as other logic functionality which enables the DSP to monitor the pupillometer control lines for either the "start" function or "data retrieval" function which must be accomplished in accordance with the present invention.

If data is sensed, the LCD processor converts a serial ASCII data stream from the LCD processor and displays it as text (or control codes) on the local LCD of the notebook computer. If the LCD processor senses a "start", it will keep reading bytes of video data from the pupillometer scanner and store them in RAM.

When the RAM has a full video picture stored thereon, the LCD processor transforms the video data into a graphical format suitable for the LCD display 50 and then the LCD processor writes the image to the LCD display 50. In a further preferred embodiment, the DSP includes initialization software for peripherals which may be attached to the pupillometer and implements a transformation algorithm to convert the video data to a graphical form suitable for the LCD 50.

More preferably, the DSP also includes a software code to interpret the ASCII data and translate this data to recognizable characters on the LCD display 50. Still more preferably, the LCD processor also comprises a latch circuit to allow the DSP to communicate with the LCD circuit 50, and a power supply which generates the negative voltage required to drive the LCD display 50.

FIG. 3 illustrates the appearance of LCD display 150 when displaying the pupil image 160 and when displaying text 180. The spots 170 are reflections of the infrared diodes 100 from the cornea of the subject's eye. The text illustrated in 180 is only one of a multitude of possible sets of data characterizing pupil size and dynamic response to a light stimulus. Further examples with a key to abbreviations used are in FIGS. 6A to 6J. As will be apparent to one skilled in the art, the LCD display 150 can be used to display text, or a graphical characterization of pupil size and dynamic response. The same or more elaborate data or graphics may be displayed on the monitor of the host computer.

Referring to FIG. 4, the hand-held pupillometer 10 is interfaced through a serial data interface 190 to a PCMCIA driver board shown generally at 200 which is placed in a laptop computer, notebook computer, or personal-type computer. The PCMCIA driver board implements a FIFO routine which drives the pupillometer 10 to produce an image that splayed on the LCD display 50 so that the user can center the pupil image on the LCD display 50 and therefore on the pupillometer. The FIFO board is preferably interfaced on a small laptop computer or notebook which has other appropriate software as described in the aforementioned Carter '506 patent to characterize pupil response and to provide analysis of the image.

In operation of the PCMCIA and FIFO board (FIGS. 5L through 5Q, and 5A through 5E respectively), these circuits reduce the number of components required to operate the pupillometer by transforming data to computer RAM directly rather than storing data representing the pupil image in a memory device on the PCMCIA driver board. Thus, the FIFO circuit in the laptop captures the pupil image directly instead of storing it on the PCMCIA interface board. In order to accomplish this result without the need for "direct memory access" (DMA) having associated timing problems, a 256 byte FIFO, the AMD 7200 Z2 unit, provides temporary storage for up to 256 bytes. It also provides a "half-full" signal, HFULL. The computer program preferably polls the HFULL signal and removes 128 bytes in one group, then checks the HFULL line again. It is only necessary that the computer be able to remove the bytes by that process a little faster than the image scanner transmits them. The pixel bits, DAT, are assembled into bytes by the 74LS164, Z3, shift register, shifted by a/DAV pulse as in the other boards, and loaded into the FIFO directly by an/EOB pulse. The byte rate is about 0.33 MHz for a 3.0 microsec time between bytes. This requires an IBM/AT or/386 I/O clock rate of 10 MHz or higher.

The I/O address decode and selection system consists of the Z4 PAL20L8 PAL and P3 jumper block. The two 8-bit DACs, Z5 and Z6, are connected directly to the computer data bus, instead of through the PAx and PBx ports of an 8255 interface unit. The PCx interface port functions have been designed into a Z1 EMP5032 Altera unit along with the timing functions supplied by the 8253 microprocessor-Control of the infrared diode excitation is accomplished by the Z6 DAC. The Z5 DAC similarly controls the stimulus diode current.

The DAC outputs drive the dual OP-AMP Z8 (LF353) and the Q1, Q2 transistors which with the feedback current sensors, R13 and R18, provide the diode currents demanded by the DAC inputs. The 20L8 PAL of the FIFO board decodes the A0 through A9 addresses to select one of the three "ports" directly, namely the/STIM for the Z5 stimulus of the PCx port functions. The/FIFOR decode is used by the computer to transfer data bytes from the FIFO. This "select" triggers the read from the FIFO output port and connects that port to the computer data bus through the tri-state buffer unit Z7.

The SCAEN, VIEW, GDDAT and AUXO pins are obtained through Z1 outputs when a/PC decode is received from Z4. The D0 through D6 and D4 data lines are bidirectional, serving as inputs and outputs. The/STRTC and SW1 are D4 and D5 inputs respectively. An "end of scan" input is not needed for the FIFO system, since the computer knows when to finish accepting data from a scan. The FIFO HFULL signal is necessary and is connected as a D3 input. Another FIFO output, the EMPT or "empty signal", is connected as a D6 input. The/PC select from the Z4 PAL addresses this port and with a simultaneous IOW output write pulse from the computer loads the D0 through D5 data into the five output latches. A /PC select with an output read pulse, /IOR, will connect the four inputs to the D3 through D6 computer data lines.

A crystal controlled clock Z1 with the XT1 32 KHz crystal capacitors $C_1$ and $C_2$, and resistors R21, R22 and R2 generates the "clock" signal for control counters in Z1, which provide the strings of START pulses at either 10 or 20 per sec. selected by the 520_10 (fifth) latched output discussed above. The D4 bit of the computer data bus supplies the input to that latch. The user of the pupillometer 10 thus initially centers the pupil image 60 with viewing bore 40 and examines the image on LCD display 50 to center the pupil image 60 on the display. When the user is satisfied that the image is centered, he or she operates a switch on handle 30 to actuate the pupillometer and to obtain a dynamic image of the pupil 160. These accurate and clear images have not heretofore been achieved in the art.

There have thus been described certain preferred embodiments of hand-held pupillometers provided in accordance with the present invention. While preferred embodiments have been described and disclosed, it will be recognized by those with skill in the art that modifications are within the true spirit and scope of the invention. The appended claims are intended to cover all such modifications.

What is claimed is:

1. A portable, hand-held pupillometer for characterizing a subject's pupil and which is operated by a user comprising:
   a hand-held optical unit for dynamically imaging the subject's pupil; and
   an electronic centering unit interfaced to the optical unit and operated by the user for centering the subject's pupil on the optical unit in preparation for imaging the subject's pupil.

2. The portable hand-held pupillometer recited in claim 1 further comprising printed circuit board means interfaced to the hand-held optical unit for driving the optical unit to dynamically image a subject's pupil.

3. The portable hand-held pupillometer recited in claim 2 wherein the printed circuit board means is a PCMCIA printed circuit board.

4. The hand-held pupillometer recited in claim 3 further comprising a scanning circuit for providing serial data which is indicative of the subject's pupil.

5. The hand-held pupillometer recited in claim 4 further comprising a centering unit display circuit interfaced to the scanning unit which receives serial data from the scanning unit indicative of the subject's pupil.

6. The hand-held pupillometer recited in claim 3 wherein the PCMCIA circuit board implements a first-in-first-out data scheme to obtain a pupil image.

7. The portable hand-held pupillometer recited in claim 6 further comprising a laptop computer in which the PCMCIA circuit card resides and which drives the pupillometer.

8. The portable hand-held pupillometer recited in claim 1 wherein the centering unit comprises a liquid crystal display.

9. The hand-held pupillometer recited in claim 8 wherein the hand-held optical unit comprises a plurality of diodes and a viewing bore through which the user views the subject's pupil.

10. A system for dynamically imaging a subject's pupil comprising:
    hand-held optical unit means for dynamically imaging the subject's pupil;
    centering means interfaced to the optical unit means and operated by a user of the system for centering the subject's pupil on the optical unit means in preparation for imaging the subject's pupil; and
    printed circuit board means interfaced to the hand-held optical unit means for driving the optical unit means to dynamically image the subject's pupil.

11. The system recited in claim 10 further comprising a computer in which the printed circuit board means is interfaced to drive the system.

12. The system recited in claim 11 wherein the printed circuit board means is a PCMCIA printed circuit card.

13. The system recited in claim 12 wherein the centering means is an LCD display.

14. The system recited in claim 13 wherein the hand-held optical unit means further comprises a set of diodes to provide illumination to produce a pupil image, and a viewing bore through which the user can view the subject's pupil.

15. The system recited in claim 14 wherein the diodes are infrared-emitting diodes.

16. The system recited in claim 15 further comprising a scanning unit interfaced to the centering means for controlling pupil image data gathering, an LCD processor for receiving serial data from the scanning unit, and first-in-first-out processing means for driving the pupil data gathering.

17. A method of characterizing a subject's pupil comprising the steps of:

viewing the subject's pupil by a user with a hand-held optical unit;

electronically displaying the subject's pupil on the hand-held optical unit;

centering the subject's pupil by the user on the hand-held optical unit; and imaging the subject's pupil on the hand-held optical unit, thereby characterizing the subject's pupil.

18. The method recited in claim 17 further comprising the step of initially centering the pupil by the user with a viewing bore provided on the hand-held optical unit.

19. The method recited in claim 18 further comprising the step of gathering data from the pupil image in response to imaging.

20. The method recited in claim 19 further comprising the step of scanning the pupil with infrared radiation to gather data from the pupil with reflected infrared radiation.

* * * * *